United States Patent [19]
Mehta

[11] Patent Number: 5,879,879
[45] Date of Patent: Mar. 9, 1999

[54] CIS-ACTING ELEMENT IN THE HUMAN LDL RECEPTOR PROMOTER AND USES THEREOF

[75] Inventor: Kamal D. Mehta, Little Rock, Ark.

[73] Assignee: The University of Arkansas for Medical Sciences, Little Rock, Ark.

[21] Appl. No.: 761,243

[22] Filed: Dec. 6, 1996

[51] Int. Cl.$^6$ .......................... C12N 15/11; C12N 15/63; C12N 15/67; C12Q 1/00
[52] U.S. Cl. .......................... 435/4; 435/69.1; 435/91.4; 435/320.1; 536/24.1
[58] Field of Search ................................ 536/24.1; 435/4, 435/320.1, 69.1, 91.4

[56] References Cited

U.S. PATENT DOCUMENTS 5,580,722  12/1996  Foulkes et al. .............................. 435/6

OTHER PUBLICATIONS

Streicher et al., J. Biol. Chem. 271(12):7128–7133 (1996).
Südhof et al., Science 228:815–822 (1985).

Primary Examiner—Johnny F. Railey, II
Attorney, Agent, or Firm—Benjamin Aaron Adler

[57] ABSTRACT

The present invention provides a novel cis-acting regulatory element that is required for maximal induction of the human low density lipoprotein (LDL) receptor gene following depletion of cellular sterols in HepG2 cells. In vivo dimethyl sulfate footprinting of the human LDL receptor promoter before and after transcriptional induction in HepG2 cells revealed protection of the sequence 5'-GAGCTTCACGGGTTAAAAAG-3' (SEQ ID NO.1), corresponding to nucleotides −126 to −145, (referred to as FP1). Further, presence of the FP1 sequence resulted in significant enhancement of luciferase reporter gene expression (approximately 375%) in response to low levels of sterols in HepG2 cells using promoter luciferase constructs. In addition, the enhancement was markedly attenuated on nucleotide substitutions within the FP1 site. Thus, the present invention discloses a novel regulatory element, FP1, in the human LDL receptor promoter and a vector containing this element. It is contemplated that FP1 can be used to confer sterol regulatory capability to heterologous genes ordinarily not under sterol regulation and be used in an assay to screen for compounds capable of stimulating cells to synthesize LDL receptors.

10 Claims, 13 Drawing Sheets

```
                                                              FP2
T CTTCACCGGA GACCCAAATA CAACAAATCA GTCGCCTGCC CTGGCGACAC TTCGAAGGA
-220            -200                            -180

FP1
CTGGAGTGGG AATCAGAGCT TCACGGGTTA AAAAGCCGAT GTCACATCGG CCGTTCGAA
-160            -140                            -120

Sp1                                     SRE-1              Sp1
CTCCTCCTCT TGCAGTGAGG TGAAGACATT TGAAAATCAC CCCACTGCAA ACTCCTCCCC
-100            -80                             -60

CTGCTAGAAA CCTCACATTG AAATGCTGTA AATGACGTGG GCCCC         (SEQ ID No.2)
-40             -20                             +1
```

FIGURE 1

```
                                                              -120
                                        -140                   o
                  -160                   oo                   ooo
       -180        oo                    oo
        o          ooo
        o
5'-AACAAATCAGTCGCCCTGCCCTGGCGACACTTTCGAAGGACTGGAGTGGGAATCAGAGCTTCACGGGTTAAAAAGCCGATGT 3'-TTGTTTAGTCAGCGGGACGGGACCGCTGTGAAAGCTTCCTGACCTCACCCTTAGTCTCGAAGTGCCCAATTTTTCGGCTACA
              FP2                                                  FP1
                                                              (SEQ ID No. 26)
```

FIGURE 3C

| Oligo Pair | -146                                                                -119 | |
|---|---|---|
| A | 5'-AGAGCTTCACGGGTTAAAAGCCGATGT-3' | (SEQ ID No. 21) |
| B |                 tt            aa           | (SEQ ID No. 22) |
| C |                 tttggcccctaa               | (SEQ ID No. 23) |
| D | | |
| E | | |
| CArG (SeRE) | GGATGTCCATATTAGGACATCT | (SEQ ID No. 24) |
| GArC | TGGGTAAGTGTGAAAAATCTGCATGTGT | (SEQ ID No. 25) |

FIGURE 5

```
Human    gcctgccctggcGacacttTcGAaGgactggGagtggGaa-tcaGAGCTTC  -225
Mouse    gaaattctgtggGaggaaTttGAgGaacttcccactGctgcggGAGCTTC  -283
Hamster  ttagatgcaaa-GtgcggTggGAtGgggaggccggaGttgcggGAGCTTC  -276
                              FP2

Human    acGGGTTAAaaaG--cCGat---GTCACATCGGCCGTTCAgAAaCTCCTCCtcttgC  -180
Mouse    tgGGGTTAAaaaGagaCGat---GTCACATCGGCCGTTCAgAAaCTCCTCCcagctC  -236
Hamster  aaGGGTTAActGtt-CGgccgtGTCACATCGGCCGTTCAgAAaCTCCTCCccgggC  -236
             FP1                                          distal Sp1

Human:    (SEQ ID No. 28)

Mouse:    (SEQ ID No. 16)

Hamster:  (SEQ ID No. 17)
```

FIGURE 9

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
     ( A ) LENGTH: 20 bp
     ( B ) TYPE: nucleic acid
     ( C ) STRANDEDNESS: double- stranded
     ( D ) TOPOLOGY: linear ( i i ) MOLECULE TYPE:
     ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:1:

GAGCTTCACG GGTTAAAAAG                                                                                   20

( 2 ) INFORMATION FOR SEQ ID NO:2:

( i ) SEQUENCE CHARACTERISTICS:
     ( A ) LENGTH: 226 bp
     ( B ) TYPE: nucleic acid
     ( C ) STRANDEDNESS: double- stranded
     ( D ) TOPOLOGY: linear ( i i ) MOLECULE TYPE:
     ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:2:

TCTTCACCGG AGACCCAAAT ACAACAAATC AGTCGCCTGC CCTGGCGACA CTTTCGAAGG           60

ACTGGAGTGG GAATCAGAGC TTCACGGGTT AAAAAGCCGA TGTCACATCG GCCGTTCGAA          120

ACTCCTCCTC TTGCAGTGAG GTGAAGACAT TTGAAAATCA CCCCACTGCA AACTCCTCCC          180

CCTGCTAGAA ACCTCACATT GAAATGCTGT AAATGACGTG GGCCCC                        226

( 2 ) INFORMATION FOR SEQ ID NO:3:

( i ) SEQUENCE CHARACTERISTICS:
     ( A ) LENGTH: 27 bp
     ( B ) TYPE: nucleic acid
     ( C ) STRANDEDNESS: single- stranded
     ( D ) TOPOLOGY: linear ( i i ) MOLECULE TYPE:
     ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:3:

TGAGGGGGCG TCAGCTCTTC ACCGGAG                                                                           27

(2) INFORMATION FOR SEQ ID NO:4:

(i) SEQUENCE CHARACTERISTICS:
        (A) LENGTH: 28 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:4:

AAGGACTGGA GTGGGAATCA GAGCTTCA         28

(2) INFORMATION FOR SEQ ID NO:5:

(i) SEQUENCE CHARACTERISTICS:
        (A) LENGTH: 26 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:5:

AGTGGGAATC AGAGCTTCAC GGGTTA         26

(2) INFORMATION FOR SEQ ID NO:6:

(i) SEQUENCE CHARACTERISTICS:
        (A) LENGTH: 22 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:6:

GCCGATGTCA CATCGGCCGT TC         22

(2) INFORMATION FOR SEQ ID NO:7:

(i) SEQUENCE CHARACTERISTICS:
        (A) LENGTH: 26 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: No (iv) ANTI-SENSE: No ( v i ) ORIGINAL SOURCE:

( x i ) SEQUENCE DESCRIPTION: SEQ ID NO:7:

GCGAGGAGCA AGGCGACGGT CCAGCG  26

( 2 ) INFORMATION FOR SEQ ID NO:8:

( i ) SEQUENCE CHARACTERISTICS:
        ( A ) LENGTH: 25 bp
        ( B ) TYPE: nucleic acid
        ( C ) STRANDEDNESS: single- stranded
        ( D ) TOPOLOGY:linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:8:

ATGCTCGCAG CCTCTGCCAG GCAGT  25

( 2 ) INFORMATION FOR SEQ ID NO:9:

( i ) SEQUENCE CHARACTERISTICS:
        ( A ) LENGTH: 20 bp
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:9:

TGTCTTCACC TCACTGCAAG  20

( 2 ) INFORMATION FOR SEQ ID NO:10:

( i ) SEQUENCE CHARACTERISTICS:
        ( A ) LENGTH: 20 bp
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:10:

GGCTGGGTGA TGTTGTGGAA  20

( 2 ) INFORMATION FOR SEQ ID NO:11:

( i ) SEQUENCE CHARACTERISTICS:
        ( A ) LENGTH:20 bp
        ( B ) TYPE: nucleic acid
        ( C ) STRANDEDNESS: single- stranded (D) TOPOLOGY: linear (ii) MOLECULE TYPE:
          (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:11:

GGCCGCCTCT ACTGGGTTGA                                                                                                 20

(2) INFORMATION FOR SEQ ID NO:12:

(i) SEQUENCE CHARACTERISTICS:
          (A) LENGTH: 20 bp
          (B) TYPE: nucleic acid
          (C) STRANDEDNESS: single-stranded
          (D) TOPOLOGY: linear (ii) MOLECULE TYPE:
          (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:12:

GAAGCCATTT TCAGTGCCAA                                                                                                 20

(2) INFORMATION FOR SEQ ID NO:13:

(i) SEQUENCE CHARACTERISTICS:
          (A) LENGTH: 17 bp
          (B) TYPE: nucleic acid
          (C) STRANDEDNESS: single-stranded
          (D) TOPOLOGY: linear (ii) MOLECULE TYPE:
          (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:13:

TACAATGAGC TGCGTGT                                                                                                    17

(2) INFORMATION FOR SEQ ID NO:14:

(i) SEQUENCE CHARACTERISTICS:
          (A) LENGTH: 19 bp
          (B) TYPE: nucleic acid
          (C) STRANDEDNESS: single-stranded
          (D) TOPOLOGY: linear (ii) MOLECULE TYPE:
          (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:14:

TGAAGGTCTC AAACATGAT                                                                                                  19

( 2 ) INFORMATION FOR SEQ ID NO:15:

( i ) SEQUENCE CHARACTERISTICS:
        ( A ) LENGTH: 20 bp
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:15:

```
AAGGCCAACC GCGAGAAGAT                                                    20
```

( 2 ) INFORMATION FOR SEQ ID NO:16:

( i ) SEQUENCE CHARACTERISTICS:
        ( A ) LENGTH: 102 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:16:

```
GAAATTCTGT GGGAGGAATT TGAGGAACTT CCCACTGCTG CGGGAGCTTC TGGGGTTAAA        60
AGAGACGATG TCACATCGGC CGTTCCAAGC TCCTCCCAGC TC                          102
```

( 2 ) INFORMATION FOR SEQ ID NO:17:

( i ) SEQUENCE CHARACTERISTICS:
        ( A ) LENGTH: 103 bp
        ( B ) TYPE: nucleic acid
        ( C ) STRANDEDNESS: double- stranded
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:17:

```
TTAGATGCAA AGTGCGGTGG GATGGGGAGG CCGGAGTTGC GGGAGCTTCA AGGGTTAACT        60
GTTCGGCCGT GTCACATCGG CCGTTCGAAG CTCCTCCCCG GGC                         103
```

( 2 ) INFORMATION FOR SEQ ID NO:18:

( i ) SEQUENCE CHARACTERISTICS:
        ( A ) LENGTH: 13 bp
        ( B ) TYPE: nucleic acid
        ( C ) STRANDEDNESS: single- stranded
        ( D ) TOPOLOGY: linear (  i i  ) MOLECULE TYPE:
               ( A ) DESCRIPTION: other nucleic acid ( i i i ) HYPOTHETICAL: No (  i v  ) ANTI-SENSE: No (  v i  ) ORIGINAL SOURCE:

(  x i  ) SEQUENCE DESCRIPTION: SEQ ID NO:18:

GGGTTAAAAA GCC                                                                                                13

( 2 ) INFORMATION FOR SEQ ID NO:19:

(  i  ) SEQUENCE CHARACTERISTICS:
               ( A ) LENGTH: 13 bp
               ( B ) TYPE: nucleic acid
               ( C ) STRANDEDNESS: single- stranded
               ( D ) TOPOLOGY: linear (  i i  ) MOLECULE TYPE:
               ( A ) DESCRIPTION: other nucleic acid ( i i i ) HYPOTHETICAL: No (  i v  ) ANTI-SENSE: No (  v i  ) ORIGINAL SOURCE:

(  x i  ) SEQUENCE DESCRIPTION: SEQ ID NO:19:

TTTGGCCCCC TAA                                                                                                13

( 2 ) INFORMATION FOR SEQ ID NO:20:

(  i  ) SEQUENCE CHARACTERISTICS:
               ( A ) LENGTH: 12 bp
               ( B ) TYPE: nucleic acid
               ( C ) STRANDEDNESS: single- stranded
               ( D ) TOPOLOGY: linear (  i i  ) MOLECULE TYPE:
               ( A ) DESCRIPTION: other nucleic acid ( i i i ) HYPOTHETICAL: No (  i v  ) ANTI-SENSE: No (  v i  ) ORIGINAL SOURCE:

(  x i  ) SEQUENCE DESCRIPTION: SEQ ID NO:20:

TTTTAAAAAG AA                                                                                                 12

( 2 ) INFORMATION FOR SEQ ID NO:21:

(  i  ) SEQUENCE CHARACTERISTICS:
               ( A ) LENGTH: 28 bp
               ( B ) TYPE: nucleic acid
               ( C ) STRANDEDNESS: single- stranded
               ( D ) TOPOLOGY: linear (  i i  ) MOLECULE TYPE:
               ( A ) DESCRIPTION: other nucleic acid ( i i i ) HYPOTHETICAL: No (  i v  ) ANTI-SENSE: No (  v i  ) ORIGINAL SOURCE:

(  x i  ) SEQUENCE DESCRIPTION: SEQ ID NO:21:

AGAGCTTCAC GGGTTAAAAA GCCGATGT                                                                                28

( 2 ) INFORMATION FOR SEQ ID NO:22:

( i ) SEQUENCE CHARACTERISTICS:
        ( A ) LENGTH: 28 bp
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:22:

AGAGCTTCAC GTTTTAAAAA GAAGATGT 28

( 2 ) INFORMATION FOR SEQ ID NO:23:

( i ) SEQUENCE CHARACTERISTICS:
        ( A ) LENGTH: 28 bp
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:23:

AGAGCTTCAC TTTGGCCCCC TAAGATGT 28

( 2 ) INFORMATION FOR SEQ ID NO:24:

( i ) SEQUENCE CHARACTERISTICS:
        ( A ) LENGTH: 22 bp
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:

( x i ) SEQUENCE DESCRIPTION: SEQ ID NO:24:

GGATGTCCAT ATTAGGACAT CT 22

( 2 ) INFORMATION FOR SEQ ID NO:25:

( i ) SEQUENCE CHARACTERISTICS:
        ( A ) LENGTH: 28 bp
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No (vi) ORIGINAL SOURCE:

(xi) SEQUENCE DESCRIPTION: SEQ ID NO:25:

TGGGTAAGTG TGAAAAATCT GCATGTGT  28

(2) INFORMATION FOR SEQ ID NO:26:

(i) SEQUENCE CHARACTERISTICS:
        (A) LENGTH: 81 bp
        (B) TYPE: nucleic acid
        (C) STRANDEDNESS: double-stranded
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:26:

AACAAATCAG TCGCCTGCCC TGGCGACACT TTCGAAGGAC TGGAGTGGGA ATCAGAGCTT  60

CACGGGTTAA AAAGCCGATG T  81

(2) INFORMATION FOR SEQ ID NO:27:

(i) SEQUENCE CHARACTERISTICS:
        (A) LENGTH: 12 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:27:

GGTTAAAAAG CC  12

(2) INFORMATION FOR SEQ ID NO:28:

(i) SEQUENCE CHARACTERISTICS:
        (A) LENGTH: 99 bp
        (B) TYPE: nucleic acid
        (C) STRANDEDNESS: double-stranded
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:

(xi) SEQUENCE DESCRIPTION: SEQ ID NO:28:

GCCTGCCCTG GCGACACTTT CGAAGGACTG GAGTGGGAAT CAGAGCTTCA CGGGTTAAAA  60

GCCGATGTCA CATCGGCCGT TCGAAACTCC TCCTCTTGC  99

{{## CIS-ACTING ELEMENT IN THE HUMAN LDL RECEPTOR PROMOTER AND USES THEREOF

FEDERAL FUNDING LEGEND

This invention was produced in part using funds obtained through a grant from the National Institutes of Health. Consequently, the Federal Government has certain rights in this invention.

BACKGROUND OF THE INVENTION

1. Field of the Invention

The present invention relates generally to molecular biology and physiology. More specifically, the present invention relates to a novel regulatory element in the human LDL receptor promoter, designated FP1, which can be used to confer sterol regulatory capability to heterologous promoters and structural genes, or to screen for compounds capable of stimulating LDL receptor synthesis in a cell.

2. Description of the Related Art

Low density lipoprotein (LDL) receptor is a key component of the mechanism by which animal cells maintain balanced cholesterol homeostasis. The transcription of the LDL receptor gene is maintained under tight feedback regulation by cellular levels of sterols (Brown, M. S., and Goldstein, J. L., *Science* 232:34–47 (1986); and Goldstein, J. L., and Brown, M. S., *Nature* 343:425–30 (1990)). In cells with excess sterols, transcription is repressed; in contrast, transcription is accelerated in cells requiring cholesterol. This feedback regulation is most important in vivo in the liver. Ingestion of cholesterol in the diet decreases hepatic levels of the LDL receptor mRNA, and consequent decline in the hepatic LDL receptor causes LDL to accumulate in the circulation (Sorci-Thomas, M., et al., *J. Biol. Chem.* 264:9039–45 (1989); Mehta, K. D.,et al.,*J. Biol. Chem.* 266: 10406–14 (1991); and Chang, R., et al., *Biochem. Biophys. Res. Commun.* 218:733–739 (1996)).

The target for sterol regulation lies within a stretch of 10 nucleotide base pairs that has been designated sterol regulatory element-1 (SRE-1) (Dawson, P. A., et al., *J. Biol. Chem.* 263:3372–79 (1988); and Smith, J. R., et al.,*J. Biol. Chem.* 265:2306–10 (1995)). In addition to SRE-1, there are two Sp1-like sequences in the human LDL receptor gene promoter which bind to purified Sp1 (Mehta, K. D.,et al.,*J. Biol. Chem.* 266:10406–14 (1991); Dawson, P. A., et al., *J. Biol. Chem.* 263:3372–79 (1988); and Kadonaga, J. T., et al., *TIBS* 11:20–23 (1986)). SRE-1s bind to SRE-1 binding proteins, which undergo proteolytic cleavage at the C-terminal membrane-associated domain (125 kDa) and are converted to functionally active nuclear forms (68 kDa) (Wang, X., et al, *Cell* 77:53–62 (1994); Sheng, Z., et al., *Proc. Natl. Acad. Sci. USA* 92:935–38 (1995); and Yokoyama, C., et al., *Cell* 75:187–97 (1994). The nuclear form of SRE-1 binding protein is transcriptionally active because it contains an acidic transcriptional activation domain and a basic helix-loop-helix leucine zipper region that mediates protein dimerization and DNA binding. All essential nucleotides of SRE-1 and Sp1 sites are conserved in evolution (Mehta, K. D.,et al., *J. Biol. Chem.* 266: 10406–14 (1991)).

In addition to regulation of the LDL receptor gene by cellular cholesterol levels, transcription is modulated by a variety of mitogenic and nonmitogenic signals in multiple cell types. Insulin and platelet-derived growth factor can stimulate LDL receptor gene transcription in quiescent mesenchymal cells (Mazzone, T., et al., *J. Biol. Chem.* 264:1787–92 (1989); Mazzone, T., et al., *J. Biol. Chem.* 265:5145–49 (1990); and Wade, D. P., et al., *Eur. J. Biochem.* 181:727–31 (1993)). Serum factors stimulate LDL receptor gene transcription in HepG2 cells, and mitogenic stimulation increases LDL receptor gene transcription in lymphocytes (Cuthbert, J. A., *J. Lipid Res.* 31:2067–78 (1990); and Ellsworth, J. L., et al., *J. Cell Physiol.* 135:213–23 (1988)). Additionally, cAMP, protein kinase C agonists, calcium ionophores, and arachidonic acid metabolites have been shown to affect LDL receptor expression in HepG2 cells (Auwerx, J. H., et al, *Proc. Natl. Acad. Sci. USA* 86:1133–37 (1989); Auwerx, J. H., et al., *Mol. Cell. Biol.* 9:2298–2302 (1989); and Krone, W., et al., *J. Lipid Res.* 29:1663–69 (1988)), and cytokines have been shown to modulate the LDL receptor pathway activity in endothelial cells, arterial smooth muscle cells, and HepG2 cells (Hamanaka, R., et al.,*J. Biol. Chem.* 267:13160–65 (1992); Nicholson, A. C., and Hajjar, D. P., *J. Biol. Chem.* 267:25982–87 (1992); and Stopeck, A. T., et al., *J. Biol. Chem.* 268:17489–94 (1993)). Many of these stimuli increase the LDL receptor transcript, and some have been shown to enhance LDL receptor gene transcription. Induction of LDL receptor gene transcription by platelet-derived growth factor and insulin have been ascribed to the participation of Sp1 and SRE-1 sequences, respectively (Basheeruddin, K., et al., *Arterioscler. Throm. Vasc. Biol.* 15:1248–54 (1995); and Streicher, R., et al.,*J. Biol. Chem.* 271:7128–33 (1996)). The mechanisms by which LDL receptor gene transcription respond to a variety of other humoral signals are not clearly understood.

The prior art is deficient in the lack of a novel regulatory element in the human LDL receptor promoter, designated FP1 used to confer sterol regulatory capability to previously known promoters and structural genes, and to screen for compounds capable of stimulating synthesis of LDL receptors in a cell. The present invention fulfills a long-standing need and desire in the art.

SUMMARY OF THE INVENTION

In the studies leading to the present invention, a novel regulatory element in the promoter of the gene for the human LDL receptor gene that is required for maximal induction of the receptor gene following depletion of sterols has been identified by both in vivo and in vitro approaches. Maximal induction of the LDL receptor gene may result from synergistic interactions of the nuclear factor(s) binding to this regulatory element with the other known transcription factors Sp1 and SRE-1 binding proteins involved in controlling LDL receptor expression in the animal cell.

Thus, the present invention discloses a novel regulatory element in the human LDL receptor promoter, designated FP1. FP1 may be used to confer sterol regulatory capability to previously known promoters and structural genes, or to screen for compounds capable of stimulating synthesis of LDL receptors in a cell.

One object of the present invention is to provide an isolated DNA molecule encoding an FP1 enhancer having a sequence SEQ ID No. 1.

An additional object of the present invention is to provide a vector containing a DNA molecule encoding an enhancer having a sequence SEQ ID No. 1, a promoter, and a heterologous gene.

Yet another object of the present invention is to provide a method for determining an ability of a test compound to stimulate a host cell to produce a detectable signal, comprising the steps of: providing a vector containing an FP1 enhancer having a sequence SEQ ID No. 1, a promoter, and a reporter gene under the transcriptional control of both said FP1 enhancer and said promoter, wherein said reporter gene is capable of conferring a detectable signal to said host cell; transfecting said vector into said host cell; culturing said host cell in the presence of a sterol so as to suppress production of said signal by the host cell; contacting said sterol-suppressed cell with a test compound to determine an ability of said test substance to stimulate said host cell to produce said signal in the presence of said sterol; and assaying for the signal to determine said ability of a test compound to stimulate said host cell to produce said detectable signal. Embodiments of this object of the invention include having a reporter gene that is an enzyme. A preferred embodiment includes having a reporter gene that is selected from the group of luciferase and β-galactosidase. Another embodiment of the present invention includes having the promoter be an LDL receptor promoter, and having the sterol used be 25-hydroxycholesterol and cholesterol. In yet another embodiment of the present method, the host cell is a liver cell.

Another object of the present invention is to provide a method for treating hypercholesteria comprising administration of said test compounds identified in the method of claim 4 as stimulating host cells to produce detectable signal to an individual to be treated.

In yet another object of the present invention, there is provided a method for conferring sterol regulatory capability to known heterologous genes, comprising the step of constructing a vector containing an FP1 sequence having a sequence SEQ ID No. 1, an LDL receptor gene promoter, and a heterologous gene under the transcriptional control of both said FP1 sequence and said LDL receptor gene promoter.

In yet another object of the present invention, there is provided a method of using the FP1 sequence to purify nuclear factor(s) binding to this site and thereby increasing LDL receptor levels. Because the promoter of the present invention is a unique enhancer for the LDL receptor, identification of this site allows screening of pharmacologic agents which will specifically increase LDL receptor levels without disturbing the regulation/levels of genes involved in the cholesterol biosynthetic pathway.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the nucleotide sequence of the human LDL receptor gene promoter analyzed for in vivo protein-DNA interactions. The major transcription initiation site is numbered as +1. The locations of both Sp1 sites, SRE-1, and FP 1 and FP 2 sequences are underlined.

FIGS. 3A–C shows the results of in vivo dimethyl sulfate footprinting of the human LDL receptor gene promoter in HepG2 cells. Footprinting areas of interest are bracketed. FIG. 3A illustrates protein-DNA interactions within nucleotides +1 to −117 in suppressed (S) and induced (I) HepG2 cells as determined by using primers 1 to 3. On the right hand side, another gel was loaded with 25% of the same samples shown on the left and exposed for same time is shown. The right hand gel is shown to indicate hypersensitivity at −59 within SRE-1 and slightly higher protection of both Sp1 sites in the induced than in suppressed HepG2 cells. FIG. 3B illustrates protein-DNA interactions in the 5'-flanking region of the human LDL receptor promoter in the region further upstream of the distal Sp1 site (−120 to −213) under both sterol conditions. FIG. 3C shows a summary of protected Gs (indicated by open circles above nucleotide sequence) within FPs 1 and 2.

FIG. 4A. At the top is an extended map of the human LDL receptor promoter with the locations of FPs 1 and 2, the SRE-1 and Sp1 sites, and the TATA and transcription start sites. Several plasmid constructs with the luciferase gene under the control of DNA fragments spanning different portions of the −273 to +35 region of the human LDL receptor gene 5'-flanking region were tested for luciferase activity by transient transfections into HepG2 cells (see Example 4). Each construct (6 μg) was cotransfected with plasmid pSV-β-Gal (2 μg) to correct for variations in DNA uptake by the cells. Relative luciferase activity values represent luciferase/β-galactosidase enzymatic activity ratios relative to that of construct A, and are averages of at least 5 to 7 independent experiments. In the case of plasmids G and H, luciferase activity shown in brackets are relative to the parallel plasmid E; specific nucleotide substitutions are indicated in lower case letters below each diagram.

FIG. 4B. illustrates a schematic representation of the sterol-mediated regulation of LDL receptor promoter-luciferase constructs in transfected HepG2 cells. Bars represent a mean of 3 to 5 independent transfection experiments, each performed in duplicate; thin lines indicate standard deviation. HepG2 cells were transiently transfected with 6 μg of the indicated plasmid together with pSV-β-Gal (2 μg). After incubation for 20 hours in the absence of sterols (± lovastatin) or presence of 10 μg/ml cholesterol plus 2 μg/ml 25-hydroxycholesterol, the cells were harvested for duplicate measurements of luciferase and β-galactosidase activities. Corrected luciferase activities were calculated as described in FIG. 4A. Fold induction is the ratio of corrected luciferase activity in the absence of sterols divided by the corrected luciferase activity in the presence of sterols and is indicated on top of the bars.

FIG. 5 indicates the nucleotide sequence of the top strand of different oligo pairs used in electrophoretic mobility shift assays. Horizontal lines represent nucleotides identical with the human LDL receptor gene 5'-flanking sequence. Mutated nucleotides are shown in lower case letters. The consensus binding site for SRF, and GArC-binding factor are underlined.

FIG. 6A. electrophoretic mobility shift assay using no protein (lane 1) or 5 μg of induced HepG2 cell nuclear extract (lanes 2 to 10) with radiolabeled wild-type oligo pair A encoding the FP1 site in the presence of poly (dI-dC) as nonspecific competitor. To test for the sequence specificity of the protein-DNA complex, competition assays was performed. Binding of nuclear extract to the $^{32}$P-labeled oligo pair were assayed in the presence of indicated fold-molar amounts of unlabeled competitors. Complex I is the specific protein-DNA complex formed with oligo pair A, and complexes II and III represent non-specific binding of nuclear proteins. The position of free probe is indicated (FP). Sequences of the competing oligonucleotides are shown in FIG. 5. Lane 1, labeled oligo pair A without nuclear extract; lane 2, labeled oligo pair A with nuclear extract; lanes 3 to 6, competition analysis with indicated fold-molar excess of unlabeled oligo pair A; lanes 7 and 8, competition with unlabeled oligo pair B carrying the same mutation present in plasmid I (FIG. 4A); lanes 9 and 10, competition with unlabeled oligo pair C containing nucleotide substitutions shown for plasmid I (FIG. 4A). FIG. 6B Competition assays using oligo pair A, C, D, SeRE or GArC at the indicated molar excess. Lane 1, labeled oligo pair A minus nuclear extract; lane 2, labeled oligo pair A with nuclear extract; lane 3, excess of unlabeled oligo pair A; lanes 4 and 5, excess of unlabeled oligo pair C; lanes 6 and 7, excess of unlabeled oligo pair D; lane 8, excess of unlabeled oligo pair CArG; lane 9, excess of unlabeled oligo pair GArC.

FIG. 9 is a comparison of the nucleotide sequence of the 5'-flanking regions of the human (−187 to −88), mouse (−336 to −236), and hamster (−329 to −226) LDL receptor genes. The nucleotide positions relative to the initiator ATG codon (+1) are shown. Gaps (−) have been inserted to achieve maximum homology. Sources for the human, mouse, and hamster sequences are indicated in the text. Identical nucleotides are shown in upper case. Repeat 1, FP 1, and FP 2 are underlined.

DETAILED DESCRIPTION OF THE INVENTION

Figure 2:
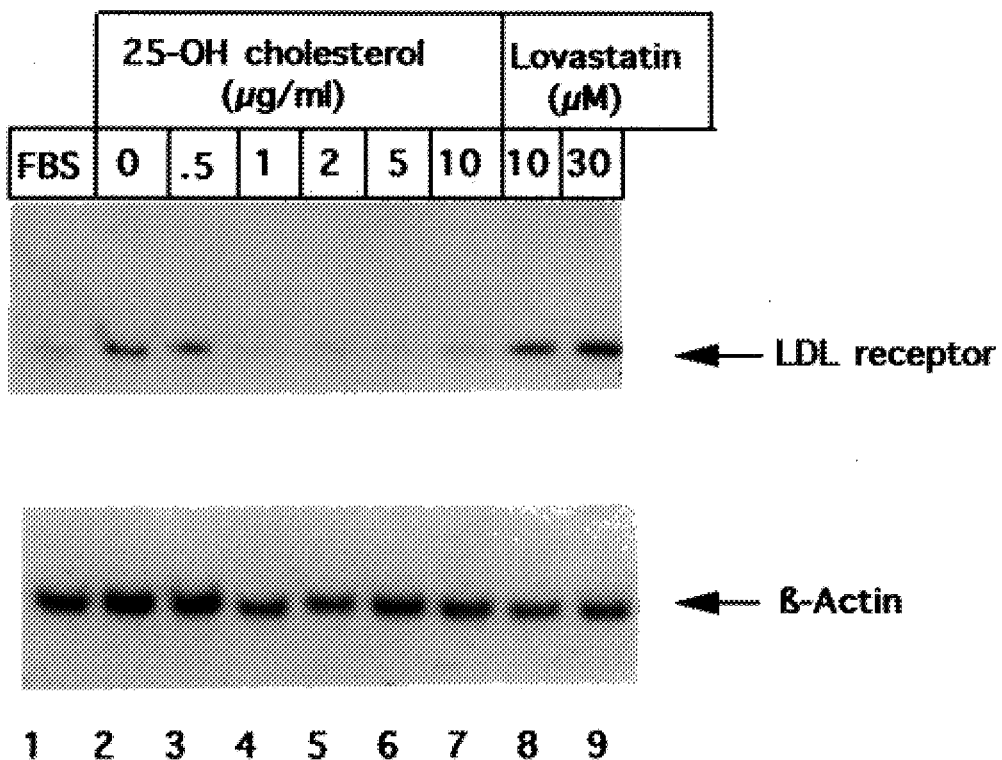
FIG. 2 shows the results of an RT-PCR analysis of LDL receptor mRNA content of HepG2 cells preincubated with FBS, cholesterol/25-hydroxycholesterol, and lovastatin. Cells were incubated for 20 hours in media containing FBS (lane 1), 10% lipoprotein deficient serum in the absence of sterols (lane 2), in the presence of different concentrations of sterols (lanes 3–7), or 10 and 30 μM lovastatin (lanes 8 and 9). Total cellular RNA was subjected to RT-PCR analysis using human LDL receptor and human β-Actin-specific primers. Primer LDLR 1, 5'-GGCTGGGTGATGTTGTGGAA-3' (+2083 to +2102) (SEQ ID No. 10), and Primer LDLR 2, 5'-GGCCGCCTCTACTGGGTTGA-3' (+1715 to +1734) (SEQ ID No. 11) were used for amplification, and Primer LDLR 3, 5'-GAAGCCATTTTCAGTGCCAA-3' (SEQ ID No. 12) was used for probing human LDL receptor-specific product. To verify that equivalent quantities of cDNA from both conditions were used in the PCR, β-Actin cDNA was used as a control. Actin 1, TACAATGAGCTGCGTGT (+312 to +329) (SEQ ID No. 13), and Actin 2, 5'-TGAAGGTCTCAAACATGAT-3' (+423 to +406) (SEQ ID NO. 14) were used for amplification, and Actin 3, 5'-AAGGCCAACCGCGAGAAGAT-3' (+377 to +395) (SEQ ID No. 15) was used for probing.

It will be apparent to one skilled in the art that various substitutions and modifications may be made to the invention disclosed herein without departing from the scope and spirit of the invention.

As used herein, the term "LDL" refers to low density lipoprotein, the major carrier of cholesterol in plasma.

As used herein, the term "LDL Receptor" refers to a protein that has a structural gene which spans ~45 kb on human chromosome 19, comprising 18 exons. The LDL receptor is a key component in the regulation of cholesterol homeostasis.

As used herein, the terms "low density lipoprotein receptor gene" or "LDL receptor gene" refer to the animal gene that codes for the low density lipoprotein receptor. In humans, the structural gene spans ~45 kb on chromosome 19 and comprises 18 exons.

As used herein, the terms "sterol regulatory element-1" or "SRE-1" refer to an element 8–10 nucleotides long in the promoter region of the LDL receptor gene. SRE-1 is also found in the promoter regions of genes for hydroxymethylglutaryl CoA reductase and hydroxymethylglutaryl CoA synthetase.

As used herein the terms "serum responsive element" or "SeRE" refer to a regulatory DNA sequence found in the promoters of immediate early genes such as fos, and is activated in response to binding of the serum response factor.

As used herein, the term "reporter gene" refers to a coding sequence attached to heterologous promoter or enhancer elements and whose product is easily and quantifiably assayed when the construct is introduced into tissues or cells.

Transcriptional and translational control sequences are DNA regulatory sequences, such as promoters, enhancers, polyadenylation signals, terminators, and the like, that provide for the expression of a coding sequence in a host cell.

As used herein, the term "oligonucleotide" refers to a molecule comprised of six or more ribonucleotides, preferably more than ten. Its exact size will depend upon many factors which, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced; i.e., in the presence of nucleotides and an inducing agent such as a DNA polymerase, and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonuclease" and "restriction enzyme" refer to bacterial enzymes, each of which cut double-stranded DNA at or near a specific nucleotide sequence.

As used herein, a cell which has been "transformed" or "transfected" refers to a cell which contains exogenous or heterologous DNA. The transforming or transfecting DNA may or may not be integrated (covalently linked) into the genome of the cell. In prokaryotes, yeast, and mammalian cells for example, the transforming or transfecting DNA may be maintained on an episomal element such as a plasmid. With respect to eukaryotic cells, a stably transformed or transfected cell is one in which the DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

The present invention is directed to a novel regulatory element, FP1, in the human LDL receptor promoter and a vector containing this element. It is contemplated that FP1 can be used to confer sterol regulatory capability to heterologous genes ordinarily not under sterol regulation and be used in an assay to screen for compounds capable of stimulating cells to synthesize LDL receptors. Alternatively, the FP1 sequence can be used as a reagent to purify nuclear factor(s) interacting with the FP 1 sequence by using affinity chromatography in order to confer high expression to the LDL receptor promoter, or FP1 sequence might be the regulator controlling LDL receptor levels in response to various cytokines and transcriptional modulators.

For therapeutic applications, a person having ordinary skill in the art of pharmacology and gene therapy would be able to determine, without undue experimentation, the appropriate dosages and routes of administration of the novel compounds capable of treating hypercholesteria of the present invention.

The experiments leading to the present invention identify a novel regulatory element in the human LDL receptor gene promoter that is necessary for maximal enhancement of the receptor gene following the depletion of sterols. The functional significance of this regulatory element is supported by the following observations: (i) sequences within the FP1 site showed specific protection from DMS attack in induced HepG2 cells, as detected by the Ligation-mediated PCR in vivo footprinting; (ii) the presence of the FP1 site resulted in an approximately 375% increase in reporter gene expression in HepG2 cells in response to sterol starvation compared to a construct without this sequence; (iii) mutagenesis of the FP1 site showed that specific nucleotide substitutions within this region abolished the enhanced expression of the reporter gene after sterol depletion without affecting the basal levels in the presence of sterols; (iv) consistent with the in vivo results, the FP1 sequence showed specific binding to a nuclear protein(s) in HepG2 cell extracts; (v) in vitro binding of oligonucleotides with specific substitutions paralleled completely the results obtained for their in vivo transcription; and (vi) alignment and comparison of the LDL receptor gene 5'-flanking sequences in different species (human, rat, and hamster) showed remarkable conservation of the position and sequence of the FP1 site.

The following examples are given for the purpose of illustrating various embodiments of the present invention and are not meant to limit it in any fashion:

EXAMPLE 1

Enzymes and Biochemicals

Standard molecular biology techniques were used (see Sambrook, J., et al., *Molecular Cloning: A Laboratory Manual*, rev. ed., vols. 1–3, Cold Spring Harbor Laboratory, Cold Spring Harbor, N.Y. (1989)). Vent DNA polymerase and restriction enzymes were purchased from New England Biolabs. 25-hydroxycholesterol and cholesterol were purchased from Sigma Chemical Company and Steraloids, Inc., respectively. Dimethyl sulfate (DMS), piperidine, and hydrazine were obtained from Aldrich Chemical Co. [$\gamma$-$^{32}$P] ATP was purchased from ICN. Antibody to serum response factor (SeRF) was purchased from Santa Cruz. DNA ligase, TRIzol, Superscript II reverse transcriptase, and all tissue culture supplies were purchased from Life Technologies. Fetal bovine lipoprotein-deficient serum was obtained from PerImmune, Inc. Zeta probe blotting membrane was purchased from BioRad. pGL2-Basic and pSV-$\beta$-galactosidase (pSV-$\beta$-Gal) vectors were purchased from Promega. The pGL2-Basic vector lacks eukaryotic promoter and enhancer sequences and contains the luciferase gene coding firefly luciferase which allows sensitive and rapid quantitation of reporter activity. A pSV-$\beta$-Gal vector was used as a positive control for monitoring transfection efficiencies of HepG2 cells. In this plasmid, SV40 early promoter and enhancer drive transcription of the lacZ gene which encodes the $\beta$-galactosidase enzyme. Dual-Light chemiluminescent reporter gene assay system for the combined detection of luciferase and $\beta$-galactosidase was purchased from TROPIX, Inc. Lovastatin was a gift from Merck, Sharp and Dohme.

EXAMPLE 2

Cell Culture

HepG2 cell line was grown routinely in Dulbecco's modified Eagle medium (DMEM) with 10% fetal calf serum (FCS) (Life Technologies). HeLa cell line was grown under identical conditions in 8% newborn calf serum. Both cell lines were grown at 37° C. in 5% $CO_2$, 95% air atmosphere.

For suppressed and induced conditions, the cells were switched to medium containing 10% lipoprotein deficient serum in the presence of either sterols (5 µg/ml 25-hydroxycholesterol plus 10 µg/ml cholesterol; Suppressed) or 30 µM lovastatin (Induced). After incubation for 16 to 20 hours, the cells were either treated with 0.1% DMS for isolation of in vivo partially-methylated genomic DNA (Becker, et al., *Cell* 51:435–43 (1987); and Rigaud, G., et al., *Cell* 67:977–986 (1991)) or used for RNA isolation (Becker-Andre, M., *Methods Enzymol.* 218:420–44 (1993); and Chomczynski, P., and N. Sacchi., *Anal. Biochem.* 162:156–59 (1987)).

EXAMPLE 3

Ligation-Mediated Polymerase Chain Reaction

Four µg of in vivo partially-methylated genomic DNA from induced and suppressed HepG2 cells was subjected to the ligation-mediated polymerase chain reaction method of in vivo footprinting essentially as described by Mueller and Wold (Garrity, P. A., and Wold, B., *Proc. Natl. Acad. Sci. USA* 89:1021–25 (1992); and Mueller, P. R., and Wold, B., *Science* 246:780–86 (1989)). The specific primers used to screen the human LDL receptor gene promoter are described below. Ligation-mediated PCRs were performed with slight modifications as follows: (i) first round denaturation was for 5 minutes at 95° C. followed by extension for 30 minutes and 10 minutes at 60° C. and 76° C., respectively; (ii) amplification was carried out using 95° C. for denaturation, 65° C. for annealing, and 76° C. for extension; and (iii) labeling reaction was done with primer 3 at 95° C. (3.5 minutes), 69° C. (2 minutes), and 76° C. (10 minutes) for 5 cycles; for primer 6, which was used to label the top strand, 95° C., 60° C., and 65° C. steps were repeated for 4 cycles. Following amplification and ethanol precipitation, DNA fragments were resuspended in 10 µl of formamide dye and 1 to 2 µl was applied onto a 8% sequencing gel. Gels were dried and exposed to Kodak X-AR film with an intensifying screen at −70° C. for 15 to 36 hours. Each of the experiments described were performed at least three times from independently methylated DNA samples, with consistent results.
Ligation-Mediated Polymerase Chain Reaction Primers:

Oligonucleotides were synthesized on an Applied Biosystems DNA synthesizer model 380B or obtained from commercial sources and gel purified prior to use. Primers 1 to 3 were utilized for scanning the region spanning the SRE-1 and both Sp1 sites (See FIG. 1 for relative positions). Primer 1: 5'-TGAGGGGGCGTCAGCTCTTCACCGGAG-3' (−236 to −210; extension reaction) (SEQ ID No. 3); Primer 2: 5'-AAGGACTGGAGTGGGAATCAGAGCTTCA-3' (−165 to −138; PCR amplification reaction) (SEQ ID No. 4); Primer 3: 5'-AGTGGGAATCAGAGCTTCACGGGTTA-3' (−156 to −131; labeling reaction) (SEQ ID No. 5). Primer 4, 5'-GCCGATGTCACATCGGCCGTTC-3' (−126 to −104) (SEQ ID No. 6). Primers 5 to 7 were utilized to scan the top strand of the promoter region farther upstream of the distal Sp1 site. Primer 5: 5'-GCGAGGAGCAAGGCGACGGTCCAGCG-3' (+123 to +98; extension reaction) (SEQ ID No. 7); Primer 6: 5'-ATGCTCGCAGCCTCTGCCAGGCAGT-3' (+76 to +52; PCR amplification reaction) (SEQ ID No. 8); Primer 7: TGTCTTCACCTCACTGCAAG-3' (−73 to −91; labeling reaction) (SEQ ID No. 9). Primers 1,2, and 4 were used to show that the footprinting patterns obtained in the induced and suppressed states are not specific to primers 1 to 3.

EXAMPLE 4

Reporter Gene Constructs

Hind III Tinkered human LDL receptor gene 5'-flanking region specific oligonucleotide was used to amplify regions of interest in the human LDL receptor gene 5'-flanking region, and the amplified fragments were subcloned in the sense orientation into the Hind III site of the pGL2-Basic vector. The sequence of the entire insert was determined by double-strand sequencing. All luciferase constructs have a common 3'-end located at +35 with respect to the start site of transcription and contain the TATA sequences and transcription start sites of the human LDL receptor gene. Plasmid DNA was isolated using Qiagen columns for transfection experiments (Qiagen, Inc.).

Cell Culture and Transient Transfection of HepG2 Cells:

For transfection experiments, HepG2 cells were seeded at $1 \times 10^6$/60-mm plate one day in advance. Transfections were performed in triplicate with 6.0 µg of DNA for each construct and 2.0 µg of pSV-β-Gal vector by the calcium chloride method. After 16 hours, the cells were washed with phosphate-buffered saline and re-fed with DMEM containing 10% FCS. Approximately one day later, transfected cells were switched to media supplemented with either 10% lipoprotein deficient serum (±lovastatin) or with 10% lipoprotein deficient serum plus 25-hydroxycholesterol/ cholesterol, and the cells were incubated for an additional 16 to 20 hours. Finally, dishes were washed with phosphate-buffered saline and lysed with 150 µl of luciferase lysis buffer (100 mM potassium phosphate, pH 7.8, 0.2% Triton X-100, and 0.5 mM dithiothreitol). Luciferase-generated light signals were detected with an automated luminometer (Model 2010, Analytical Luminescence Laboratory) using a 2 second delay and 5 second measurement, and β-galactosidase initiated light signals were measured similarly after the addition of accelerator-II. The luciferase activity was normalized to β-galactosidase activity for each plasmid. Data are expressed as the means ±standard deviation.

EXAMPLE 5

Preparation of Nuclear Extracts and Gel-mobility Shift Assays/Kinetics of Dissociation HepG2 nuclear extracts were prepared from 20 confluent 150-mm plates, and HeLa cells were grown in suspension until they reached a concentration of $3-6 \times 10^5$/ml. Nuclei were prepared from both cell lines by the method described by Dignam et al., *Nucleic Acids Res.* 11:1475–89 (1983), except that buffer A was supplemented with 1 mM dithiothreitol, 1 mM phenylmethylsulfonyl fluoride, and 1 µg each of pepstatin A and leupeptin per ml, and the nuclear extracts were prepared from nuclei as described by Gorski et al., *Cell* 47:767–776 (1986). Nuclear extracts were quick-frozen and stored in liquid nitrogen in aliquots. Protein concentrations were determined using a modified Bradford assay with bovine γ-globulin as a standard (Bio-Rad) and were typically 3–7 mg/ml. Oligonucleotides were annealed and gel-purified prior to end-labeling with T4 polynucleotide kinase in the presence of [γ-$^{32}$P]ATP. Nuclear extract (5 µg) was incubated in a final volume of 15 µl in10 mM Tris(hydroxymethyl)aminoethane (Tris), pH 7.5, 50 mM NaCl, 5% glycerol, 1 mM DTT, 1 mM ethylenediaminetetraacetic acid (EDTA), 1 mM spermidine, 1 µg of poly(dI-dC), with each probe (20,000 cpm; 0.5 to 1 ng) for 20 minutes at room temperature.

In competition analysis, extracts were incubated with the indicated molar excess of unlabeled oligonucleotides for 5 minutes prior to the addition of the labeled oligonucleotides. The DNA-protein complexes were resolved on 4.5% nondenaturing polyacrylamide gels (29:1 cross-link) in 0.25× TBE (1×TBE is 89 mM Tris, pH 8, 89 mM boric acid, and 2 mM EDTA). The gels were dried and analyzed by autoradiography using Kodak X-AR film. Dissociation kinetics were measured as described by Fried and Crothers, *Nucl. Acids Res.* 9:6505–25 (1981). Protein-DNA complexes were quantified by excising the bands and scintillation counting.

EXAMPLE 6

In Vivo Footprinting of the Human LDL Receptor Gene Promoter

Figure 3A:
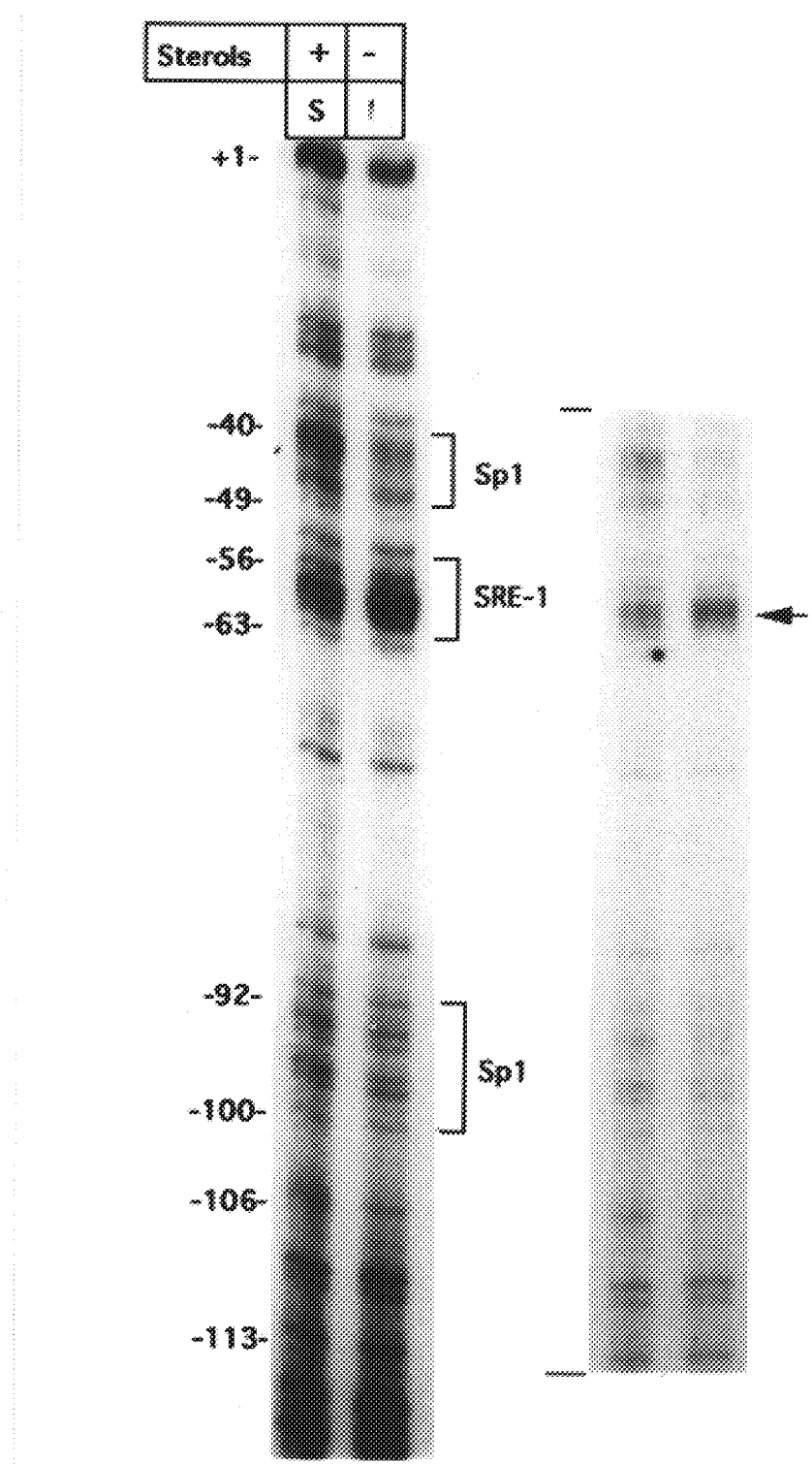

The optimal conditions for the suppressed and induced states of LDL receptor gene expression in HepG2 cells were determined by growing HepG2 cells in lipoprotein deficient serum media containing different concentrations of sterols and lovastatin, and then by quantitating the LDL receptor transcript by using the revese transcription-polymerase chain reaction (RT-PCR) method as described in Example 3 (see also Chang, R., et al., *Biochem, Biophys, Res. Commun.* 218:7633–739 (1996)). It is apparent that maximal suppression of the LDL receptor gene was obtained in lipoprotein deficient serum media with 25-hydroxycholesterol concentration above 1 μg/ml, and maximal induction was obtained with 30 μM lovastatin (see FIG. 2). To determine the occupancy status of different genetic elements under these conditions in vivo, primers (primers 1 to 3) for footprint analysis were first designed to target nucleotides −1 to −117 of the human LDL receptor promoter. G ladders from the suppressed and induced HepG2 are shown in FIG. 3A and a comparison of reactivities of G residues revealed Gs which are either protected, enhanced, or unaffected with these treatments. The SRE-1 region showed a hypersensitive G at −59, an observation consistent with earlier in vivo footprinting studies (Ellsworth, J. L., et al., *J. Lipid Res.* 36:383–92 (1995); and Lloyd, D. B., and Thompson, J. F., *J. Biol. Chem.* 270:25812–18 (1995)). However, G residues of the proximal Sp1 site (−40 to −49) and the distal Sp1 site (−92 to −100) exhibited slightly more protection from DMS attack in the induced than suppressed HepG2 cells as compared to the previous reports (Ellsworth, J. L., et al., *J. Lipid Res.* 36:383–92 (1995); and Lloyd, D. B., and Thompson, J. F., *J. Biol. Chem.* 270:25812–18 (1995)). In addition, weak protection was observed at nucleotide −106. To rule out the possibility that this selective pattern is not specific for this particular combination of oligonucleotides, a different oligonucleotide (primer 4) closer to SRE-1 was used for labeling the PCR products from an independent experiment. As expected, an identical pattern of footprinting over SRE-1 and the adjacent Sp1 site was observed (data not shown).

Figure 3B:
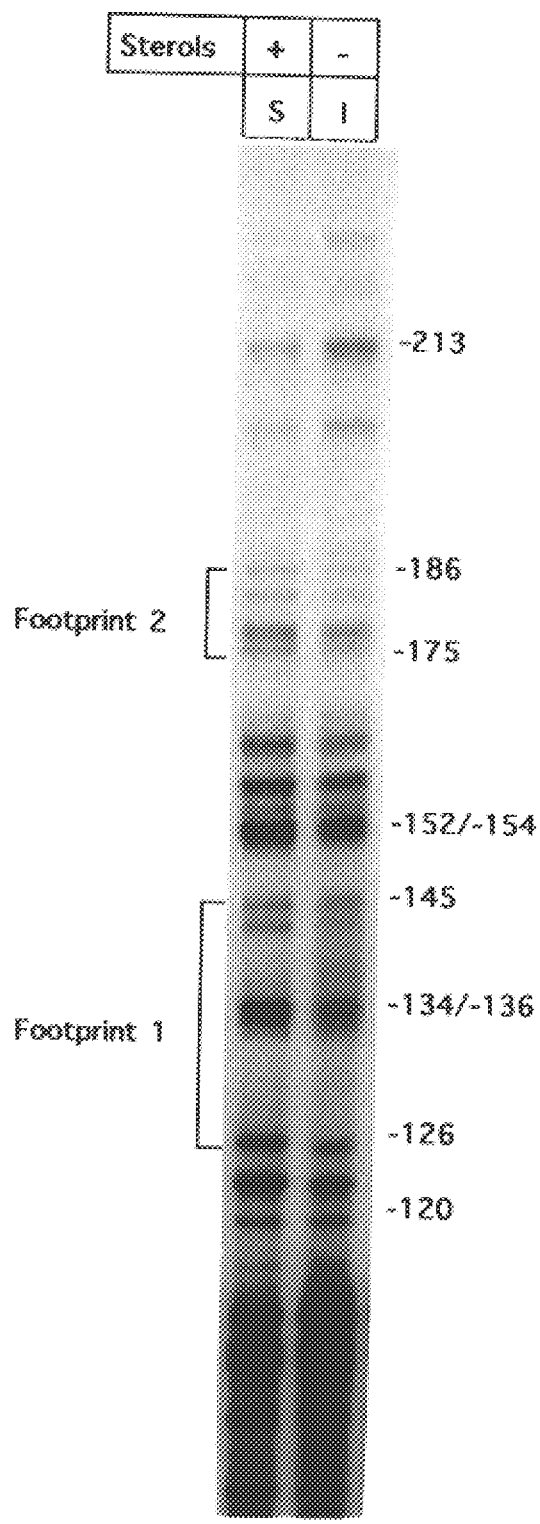

Investigation of the protein-DNA interactions in the region further upstream of these repeats using primers 5 to 7 had revealed significant protections of nucleotides from −126 to −145 (designated FP1), with a slight protection of nucleotides from −175 to −187 (designated FP2) (FIG. 3B). The protected Gs within the FP1 site included guanines at −126, −134, −135, −136, −143 and −145, whereas Gs at nucleotides −175, −177, −178, −183 and −187 were protected in the FP2 (FIG. 3C). Interestingly, the in vivo protected FP1 site (−125 to −145) coincided with the in vitro DNase I protected region (−127 to −159) observed earlier for the human LDL receptor gene promoter (Sudhof, T. C., et al., *Science* 228:815–22 (1985)). The observed in vivo footprints were very reproducible, even when slightly different.

EXAMPLE 7

Figure 4A:
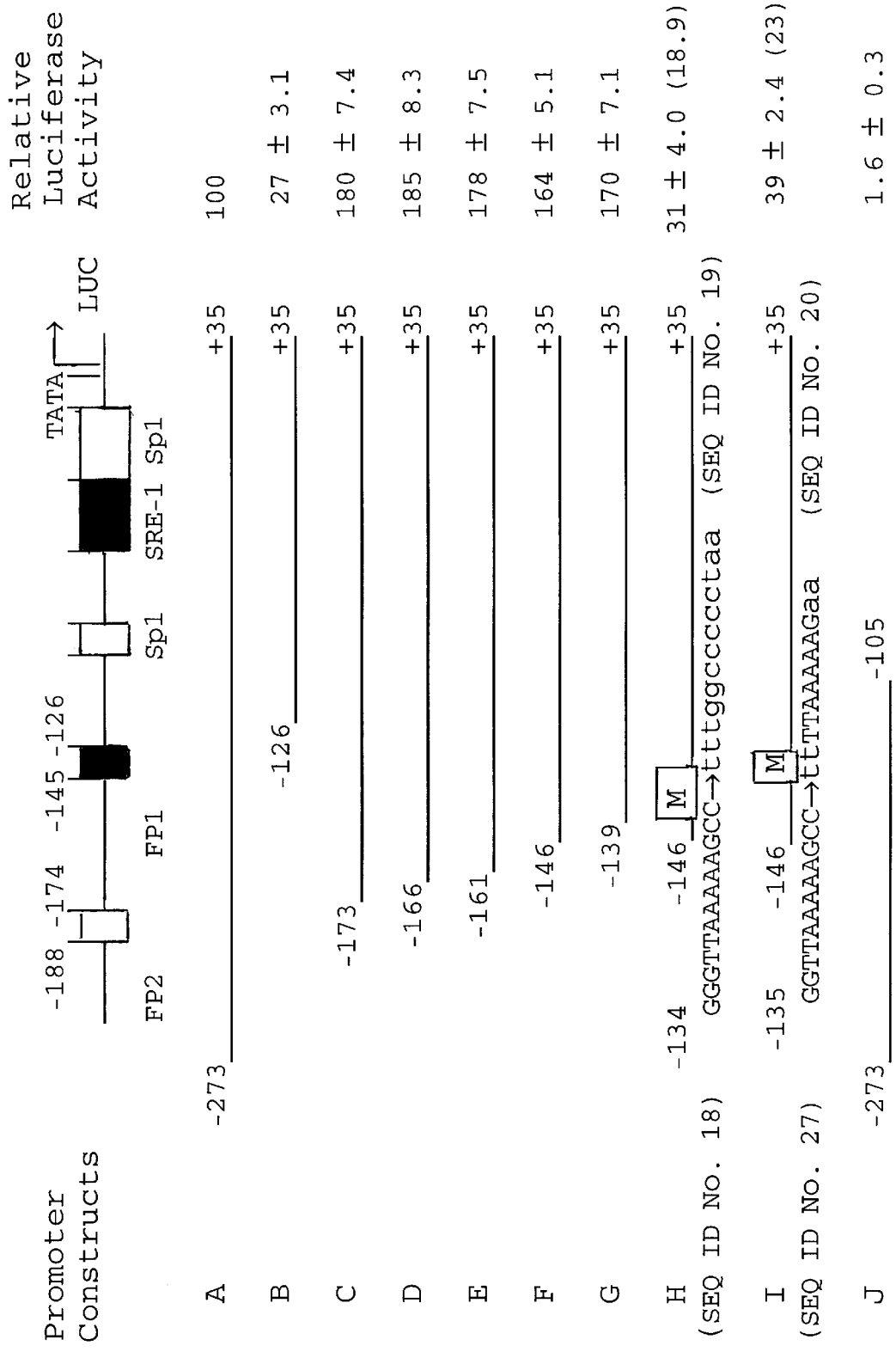
FIGS. 4A–B shows the expression of human LDL receptor promoter-luciferase fusion genes in HepG2 cells.
Figure 4B:
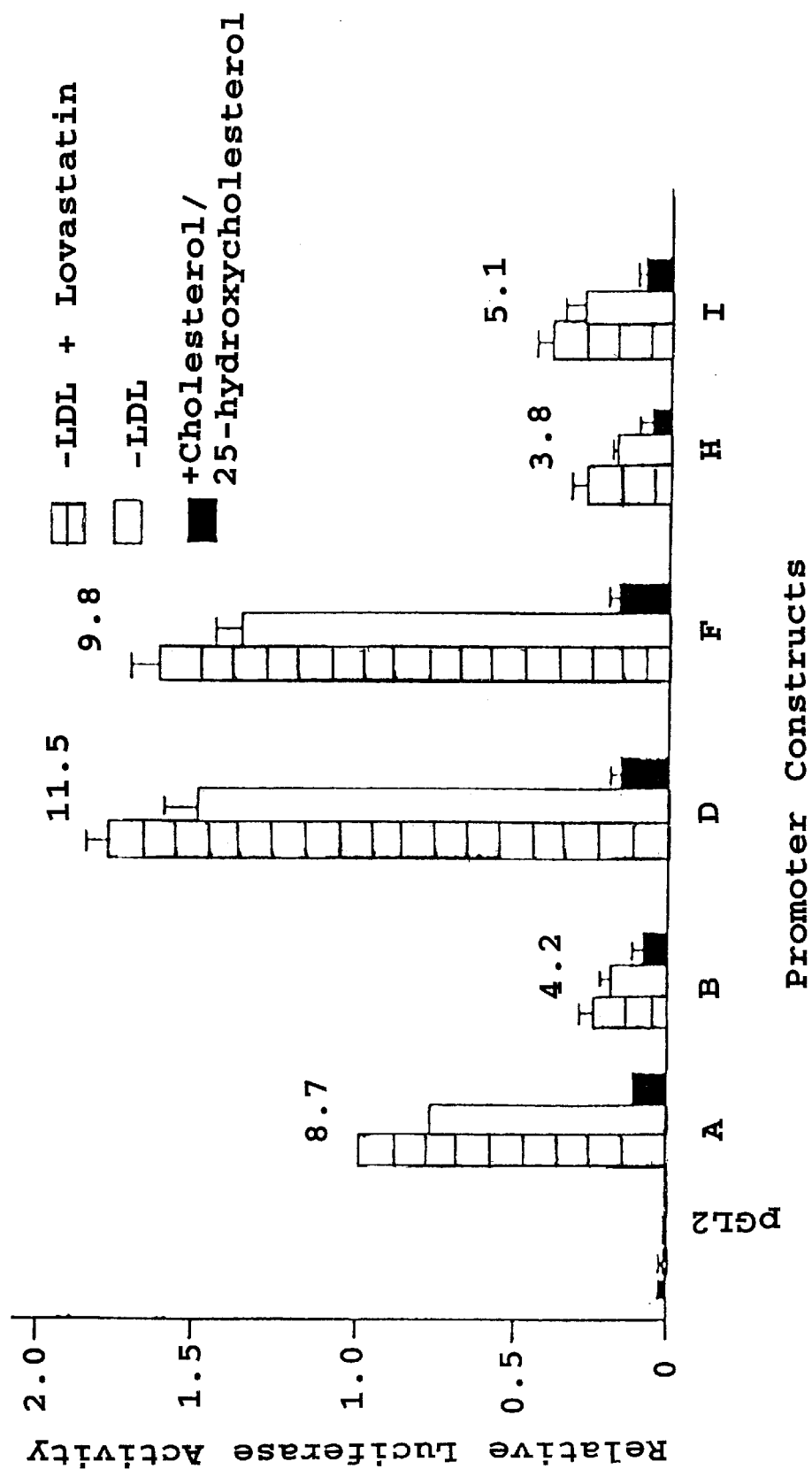

FP1 is Required for Maximal Induction of the LDL Receptor Gene in Response to Low Levels of Sterols As a first step in determining the significance of the in vivo protected sites, varying lengths of the human LDL receptor gene promoter were ligated to the 5' end of the promoterless luciferase reporter gene in plasmid pGL2-Basic. These constructs were transiently transfected into cultured HepG2 cells, the transfected cells were grown under induced and suppressed conditions for LDL receptor expression, and luciferase activity was determined as described in Example 4. The luciferase activity is expressed relative to the activity of the construct labeled A (FIG. 4A). The negative control, promoterless plasmid pGL2-Basic, consistently exhibited negligible levels of luciferase expression (FIG. 4B). The co-transfection of pSV-β-Gal control vector allowed correction of luciferase values for transfection efficiency. Transfection results demonstrated that the presence of −273 to −127 region, that includes both the FP1 and FP2 sites in a reporter construct containing the −126 to +35 sequence of the human LDL receptor promoter, resulted in at least 375% increase in luciferase expression in the absence of sterols compared to a parallel plasmid without this additional region; levels of both constructs were almost suppressed to a similar extent by sterols (compare plasmid A vs B, FIG. 4). Streicher et al., *J. Biol. Chem.* 271:7128–33 (1996), recently have reported that constructs containing a fragment that spans the −222 to +88 region of the human LDL receptor gene 5'-flanking region showed 2- to 3-fold higher reporter gene level expression compared to plasmids containing either −105 to +88 (both Sp1 sites and SRE-1) or −69 to +88 (proximal Sp1 site and SRE-1) region. These results are in agreement with the results obtained in the research of the present invention.

To identify the cis-element in more detail, a series of 5' deletion constructs without the FP2 site were prepared and transfected into HepG2 cells (FIG. 4A). As shown in FIG. 4A, deletion of sequence between −273 to −173, which includes the FP2 site, consistently resulted in an approximately 2-fold elevation in the expression of the reporter gene in the absence of sterols relative to plasmid A (compare plasmid A vs C, Fig. 4A.). Further, 5' deletions (plasmids D, E, F and G) did not affect the enhancement observed for plasmid C in response to depletion of sterols.

To delineate further the regulatory element present within −145 to −126 of promoter region, reporter plasmids were constructed with the FP1 sequence specifically changed at the nucleotide positions shown in FIG. 4 (plasmids H and I), and tested in the transient transfection assays. Introduction of transversion mutations of all the nucleotides between −134 to −146 (plasmid H) abolished the FP1-dependent enhancement in the reporter gene level. Interestingly, specific changes of four nucleotides (guanines at −135/−136 and cytosines at −145/−146 to thymines and adenines, respectively; plasmid I) also reduced drastically the ability of the FP1 region to enhance transcription. The observed reporter levels are not statistically different from the construct without the FP1 site (compare plasmid I vs B, FIG. 4A).

Fold-regulation of different constructs by sterols was tested in HepG2 cells and the results are summarized in FIG. 4B. Mostly, constructs showing higher induced levels showed a slight and insignificant elevation in the basal levels (suppressed) of the reporter gene in the presence of sterols (FIG. 4B). The above study shows that constructs containing the FP1 site without the FP2 site showed maximal regulation by sterols in HepG2 cells. Finally, the presence of both the FP1 and FP2 sites is not sufficient to elicit transcription of the reporter gene (plasmid J, FIG. 4A) since no transcription was observed with a promoter fragment containing these sequences without the other known regulatory elements of the human LDL receptor gene. These results indicate that other sequences within the −273 to −126 region contribute very little and that nearly all of the 3- to 4-fold elevation in reporter gene expression is mediated by sequences within the −139 to −126 region of the human LDL receptor gene promoter in HepG2 cells.

EXAMPLE 8

In Vitro Binding of Nuclear Factor(s) to the FP1 Sequence

Figure 6A:
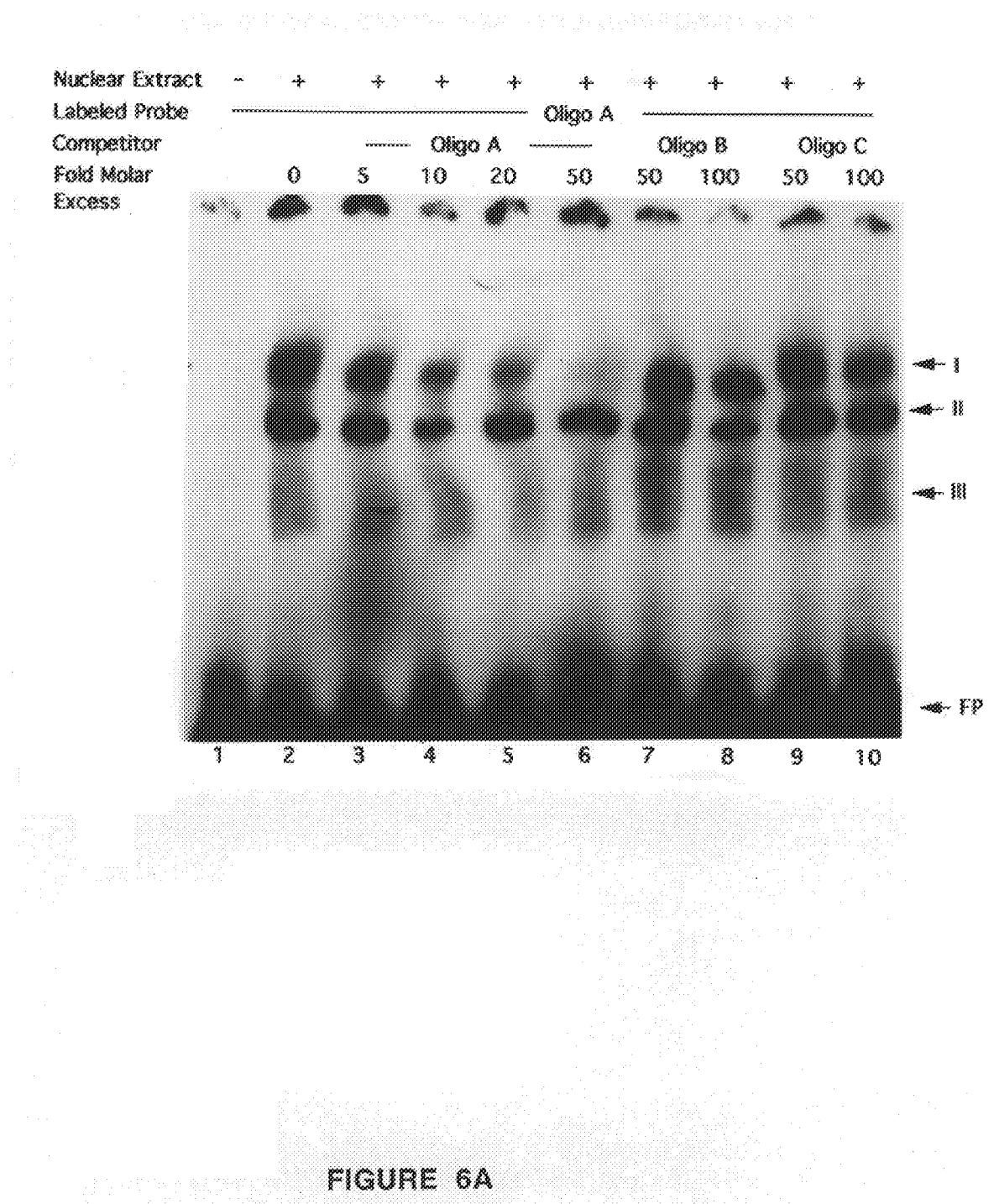
FIG. 6A–B shows the results obtained with electrophoretic mobility shift assay analysis of nuclear proteins interacting with the FP1 sequence.
Figure 6B:
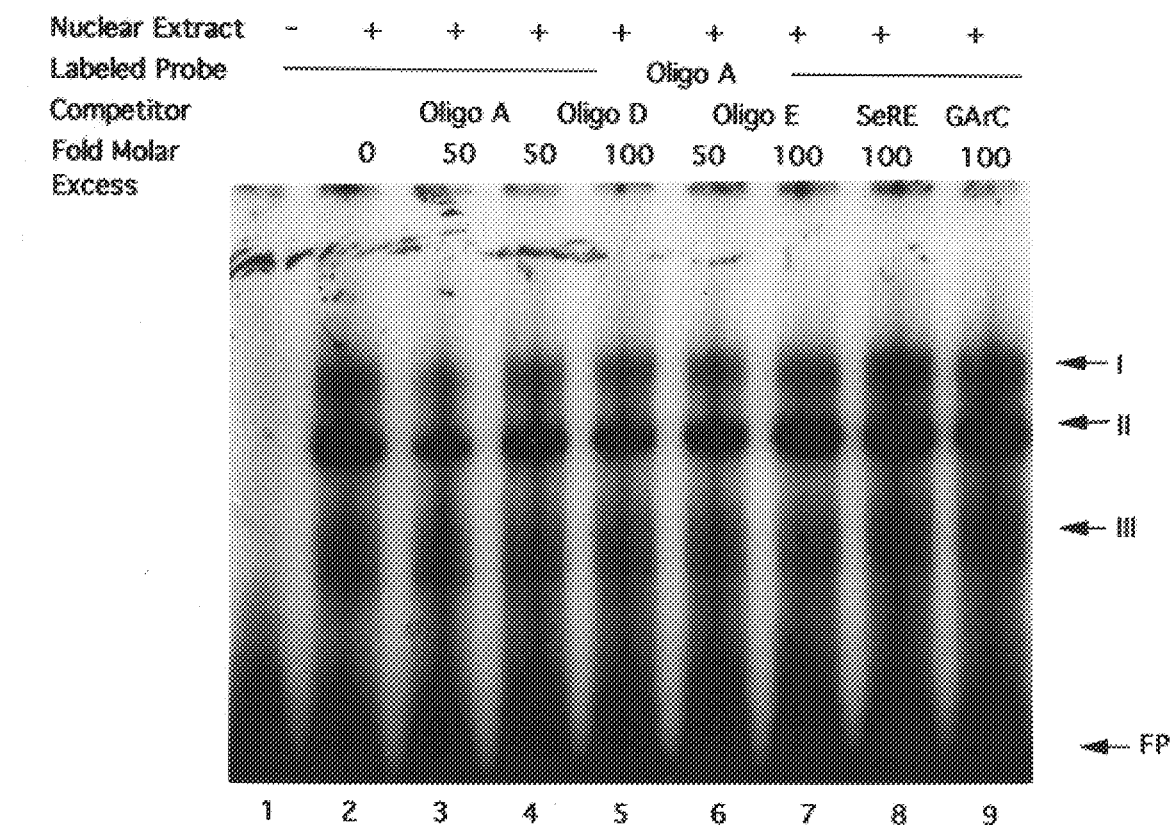

To understand the nature of the protein interactions that occur over the FP1 site, electrophoretic mobility shift assays were performed with nuclear extracts from induced HepG2 cells. Oligo pair A (nucleotides −119 to −146), which includes all nucleotides within the in vivo DMS protected region, was used in the electrophoretic mobility shift assay (see Description of Drawings, FIG. 5, for sequences of oligo pairs used). As seen in FIG. 6A, nuclear extracts from HepG2 cells produced three, slowly-migrating shift bands; labeled I, II, and III. Addition of increasing amounts of unlabeled oligo pair A competed for binding and strongly inhibited the formation of band I. In contrast, bands II and III were not competed out and thus appear to represent non-specific binding of proteins in nuclear extracts (FIG. 6A, lanes 3–6). The mutant oligo pairs B and C, containing mutations of plasmids I and H, respectively (lanes 7–10), did not compete with oligo pair A, in agreement with the transfection data shown in FIG. 4. The lack of competition of oligo pair D or E for binding to the FP1 site suggests that sequences flanking the AT-rich core are required for the binding to the FP1 sequence (FIG. 6B). In reciprocal experiments in which these sequences were tested as labeled probes, complex I did not form with the mutated or deleted oligo pairs (data not shown). Furthermore, as shown in FIG. 6B, oligo pairs corresponding to the consensus sequences of two AT-rich motifs, the CArG (c-fos; 38) and GArC (a-myosin; 39), did not compete for complex I even with a 100-fold molar excess. Thus, the above results indicate that HepG2 cells express a nuclear factor that binds specifically to the FP1 sequence and the FP1-binding activity is distinct from the earlier reported nuclear factors binding to the CArG and GArC motifs.

Figure 7:
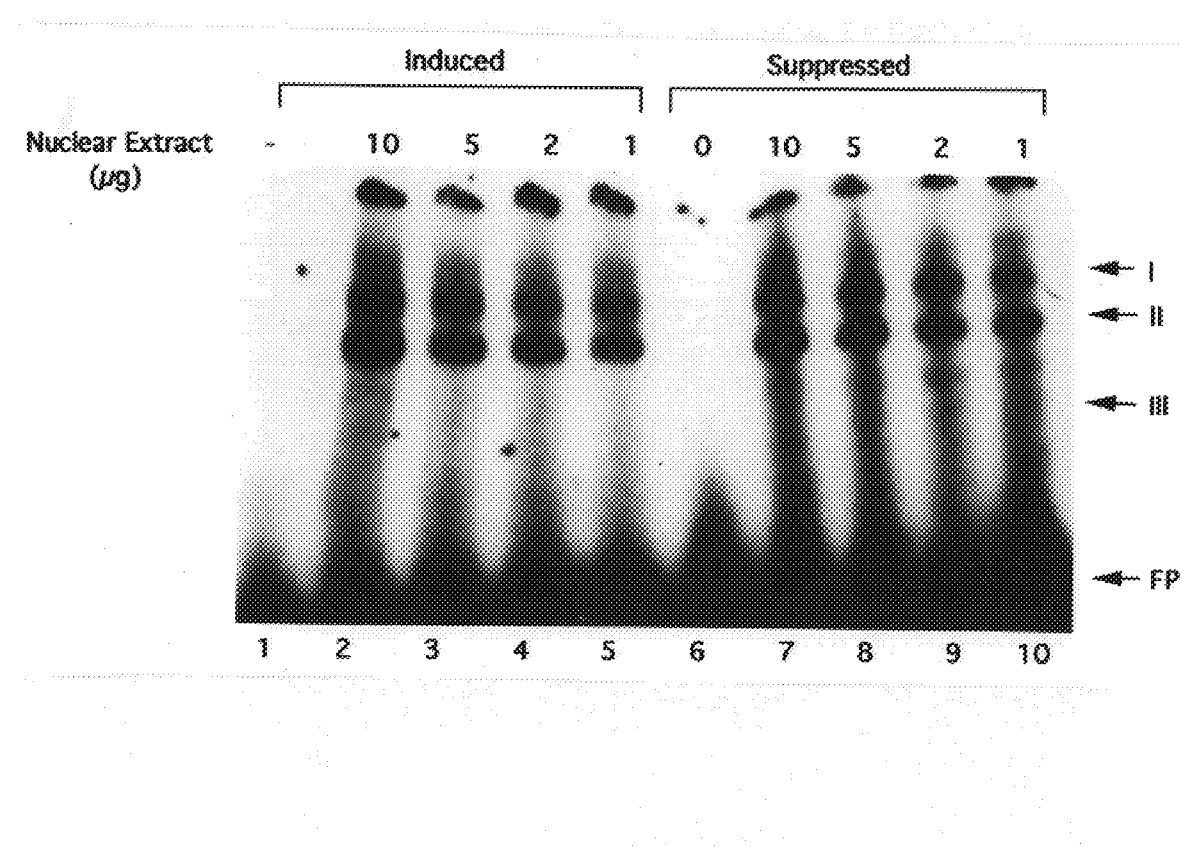
FIG. 7 shows the interaction of the FP1 sequence with nuclear proteins from induced and suppressed HepG2 cells. Electrophoretic mobility shift assays were carried out with end-labeled double-stranded oligo pair A (see FIG. 5) in the presence of nonspecific competitor poly (dI-dC) and the indicated amounts of nuclear extracts prepared from HepG2 cells starved for sterols (induced; lanes 1 to 5) or incubated with cholesterol (10 μg/ml) and 25-hydroxycholesterol (2 μg/ml) for 20 hours (suppressed; lanes 6 to 10).

Electrophoretic mobility shift assays were performed to compare the relative amounts of the FP1-binding factor in nuclear extracts of induced and suppressed HepG2 cells. To optimize comparisons between bands, different concentrations of nuclear extracts prepared from HepG2 cells were used at the same time in the binding reactions. No significant difference in the formation of the specific complex I was observed (FIG. 7).

To compare the stabilities of DNA-protein complexes involving FP1 and nuclear proteins prepared from the induced and suppressed HepG2 cells, the dissociation kinetics were compared using electrophoretic mobility shift assays. Nuclear extract was mixed with probe and binding was allowed to reach equilibrium; maximum formation of complex I was found to occur by 30 minutes. An average of 1.2-fold difference between the induced and suppressed complex I intensity that persisted from 10 minutes to 4 hours. Following the addition of unlabeled FP1 competitor to the equilibrium reaction, there was a parallel decrease in the intensity of complex I in the control and stimulated extracts with a 1.1 to 1.2-fold difference in the intensity of the band that was maintained over the time course (data not shown). The addition of nonspecific competitor oligonucleotides had no effect on complex formation or dissociation.

Figure 8:
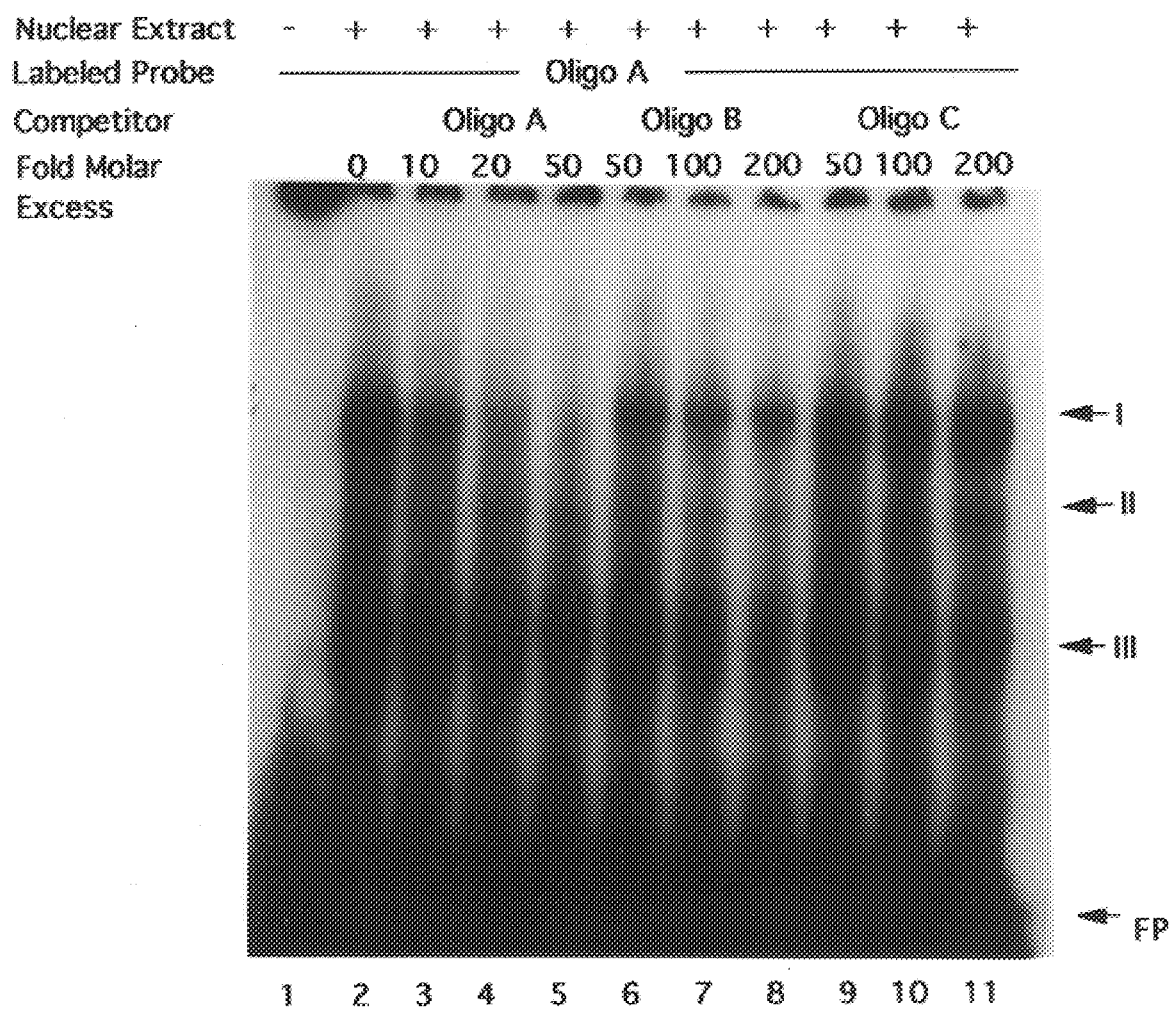
FIG. 8 shows the results of electrophoretic mobility shift assay analysis of HeLa nuclear proteins that bind to the FP1 sequence. Binding assays were performed as described in the legend of FIG. 6. Labeled oligo pair A was incubated with HeLa cell extracts in the presence of poly (dI-dC) as nonspecific competitor and the indicated molar excess of unlabeled oligo pair A, B, or C. The positions of the specific nucleoprotein/DNA complex (I) and nonspecific complexes (Complexes II and III) are indicated. Lane 1, labeled oligo pair A minus nuclear extract; lane 2, labeled oligo pair A with nuclear extract; lanes 3 to 5, excess of unlabeled oligo pair A; lanes 6 to 8, excess of unlabeled oligo pair B; lanes 9 to 11, excess of unlabeled oligo pair C.

To test whether the FP1 binding factor is specific to the hepatic cell line HepG2, electrophoretic mobility shift assays were also performed with non-hepatic HeLa nuclear extracts. When amounts of the HeLa nuclear extract similar to those used for the HepG2 cells were tested, a specific retarded band of similar electrophoretic mobility as complex I was observed (FIG. 8). Furthermore, binding specificity of HeLa nuclear protein was similar to that of HepG2 cells because unlabeled oligo pair A competed effectively in the binding assays while mutant oligo pair B or C showed no significant competitions. Similar results were also obtained for other mutant oligo pairs tested with HepG2 nuclear extract (data not shown).

Thus, the experiments leading to the present invention identify a novel regulatory element in the human LDL receptor gene promoter that is necessary for maximal enhancement of the receptor gene following the depletion of sterols. The functional significance of this regulatory element is supported by the following observations: (i) sequences within the FP1 site showed specific protection from DMS attack in induced HepG2 cells, as detected by the ligation-mediated PCR in vivo footprinting; (ii) the presence of the FP1 site resulted in an approximately 375% increase in reporter gene expression in HepG2 cells in response to sterol starvation compared to a construct without this sequence; (iii) mutagenesis of the FP1 site showed that specific nucleotide substitutions within this region abolished the enhanced expression of the reporter gene after sterol depletion without affecting the basal levels in the presence of sterols; (iv) consistent with the in vivo results, the FP1 sequence showed specific binding to a nuclear protein(s) in HepG2 cell extracts; (v) in vitro binding of oligonucleotides with specific substitutions paralleled completely the results obtained for their in vivo transcription; and (vi) alignment and comparison of the LDL receptor gene 5'-flanking sequences in different species (human, rat, and hamster) showed remarkable conservation of the position and sequence of the FP1 site (FIG. 9) (Sudhof, T. C., et al., *Science* 228:815–22 (1985); Hoffer, M. J. V., et al., *Biochem. Biophys. Res. Commun.* 191:880–86 (1993); and Bishop, R., *J. Lipid Res.* 33:551–558 (1993)). Taken together, the above experiments define a 20-bp FP1 site as a functionally relevant enhancer sequence that mediates its effect through a nuclear protein in response to the low cellular levels of sterols.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated DNA molecule encoding an FP1 enhancer having a SEQ ID No. 1.

2. A vector containing a DNA molecule encoding an enhancer having a sequence SEQ ID No. 1, a promoter, and a heterologous gene.

3. The vector of claim 2, wherein said heterologous gene is a reporter gene.

4. A method for determining an ability of a test compound to stimulate a host cell to produce a detectable signal, comprising the steps of:

providing a vector containing an FP1 enhancer having a sequence SEQ ID No. 1, a promoter, and a reporter gene under the transcriptional control of both said FP1 enhancer and said promoter, wherein said reporter gene is capable of conferring a detectable signal to said host cell;

transfecting said vector into said host cell;

culturing said host cell in the presence of a sterol so as to suppress production of said signal by the host cell;

contacting said sterol-suppressed cell with a test compound to determine an ability of said test substance to stimulate said host cell to produce said signal in the presence of said sterol; and assaying for the signal to determine said ability of a test compound to stimulate said host cell to produce said detectable signal.

5. The method of claim 4, wherein said reporter gene is an enzyme.

6. The method of claim 5, wherein said enzyme is selected from the group of luciferase and β-galactosidase.

7. The method of claim 4, wherein said promoter is an LDL receptor promoter.

8. The method of claim 4, wherein said sterol is a mixture of 25-hydroxycholesterol and cholesterol.

9. The method of claim 4, wherein said host cell is a liver cell.

10. A method for conferring sterol regulatory capability to known heterologous genes, comprising the step of constructing a vector containing an FP1 sequence having a sequence SEQ ID No. 1, an LDL receptor gene promoter, and a heterologous gene under the transcriptional control of both said FP1 sequence and said LDL receptor gene promoter.

* * * * *